(12) United States Patent
Levine et al.

(10) Patent No.: US 7,291,581 B2
(45) Date of Patent: Nov. 6, 2007

(54) BORATE ESTER LUBRICANT ADDITIVES

(75) Inventors: Jeffrey A. Levine, White Plains, NY (US); Si Wu, White Plains, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 546 days.

(21) Appl. No.: 10/848,303

(22) Filed: May 18, 2004

(65) Prior Publication Data

US 2004/0235681 A1 Nov. 25, 2004

Related U.S. Application Data

(60) Provisional application No. 60/472,390, filed on May 21, 2003.

(51) Int. Cl.
*C10M 169/06* (2006.01)
*C10M 125/26* (2006.01)
*C07F 5/02* (2006.01)

(52) U.S. Cl. .................... 508/185; 508/168; 546/13

(58) Field of Classification Search .............. 546/13; 508/168, 185
See application file for complete search history.

(56) References Cited

U.S. PATENT DOCUMENTS

| | | | |
|---|---|---|---|
| 3,505,226 A | 4/1970 | Cyba | 252/49.6 |
| 3,682,935 A | 8/1972 | Law | 260/296 |
| 4,382,006 A | 5/1983 | Horodysky | 252/49.6 |
| 4,389,322 A | 6/1983 | Horodysky | 252/49.6 |
| 4,406,802 A | 9/1983 | Horodysky et al. | 252/49.6 |
| 4,492,642 A | 1/1985 | Horodysky | 252/49.6 |
| 4,568,472 A | 2/1986 | Horodysky et al. | 252/49.6 |
| 4,741,848 A | 5/1988 | Koch et al. | 252/49.6 |
| 4,892,670 A | 1/1990 | Mendelson | 252/37 |
| 5,464,548 A * | 11/1995 | Cahoon et al. | 508/186 |
| 5,652,201 A * | 7/1997 | Papay et al. | 508/228 |
| 2002/0008465 A1 * | 1/2002 | Ueno et al. | 313/504 |

OTHER PUBLICATIONS

Farfan, N., Castillo, D., Joseph-Nathan, P., Conteras, R., Szentpaly, L. v., J. Chem. Soc. Perkin Trans. 2, 1992, 527-532.*
Hopfl, H., J. Organomet. Chem., 1999, 581, 129-149.*
Z. Zheng et al., Wear, vol. 222, (1998), pp. 135-144.

* cited by examiner

*Primary Examiner*—Vasu Jagannathan
*Assistant Examiner*—James Goloboy
(74) *Attorney, Agent, or Firm*—Tyler A. Stevenson

(57) ABSTRACT

Disclosed are borate and boronate compounds of the formulae

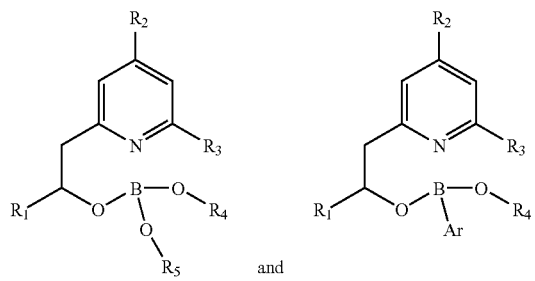

and where $R_1$, $R_2$ and $R_3$ are independently hydrogen, straight or branched chain alkyl of 1 to 24 carbon atoms, straight or branched chain alkenyl of 2 to 24 carbon atoms, cycloalkyl of 5 to 12 carbon atoms, aryl of 6 to 10 carbon atoms, aralkyl of 7 to 15 carbon atoms, alkaryl of 7 to 15 carbon atoms; Ar is substituted or unsubstituted aryl of 6 to 10 carbon atoms; and $R_4$ and $R_5$ are independently defined as for $R_1$ and may also be hydroxyphenyl or alkylated hydroxyphenyl, or $R_4$ and $R_5$ together with the —OBO— group form a substituted or unsubstituted 5 or 6 membered ring. The borate and boronate compounds are effective as antiwear, extreme pressure, and friction modifying additives for lubricating oils and fuels.

20 Claims, No Drawings

BORATE ESTER LUBRICANT ADDITIVES

This application claims benefit under 35 USC 119(e) of U.S. provisional app. No. 60/472,390, filed May 21, 2003.

The present invention is aimed at borates and boronate esters derived from boric acids or boronic acids, 2-hydroxyethylpyridines and hydrocarbyl alcohols. The present borates and boronate esters provide ashless, phosphorus-free and sulfur-free antiwear, extreme pressure friction modifiying additives for lubricating oils and fuels.

U.S. Pat. No. 4,382,006 describes ethoxylated amines and borated derivatives thereof useful as friction modifiying additives for organic fluids. U.S. Pat. No. 4,406,802 teaches borates of mixed alcohols, amides, amines, hydroxy esters, ethoxylated amines, ethoxylated amides and hydroxyalkyl, hydroxyalkenylalkyl or alkenylimidazolines.

U.S. Pat. No. 4,389,322 discloses ethoxylated amids and borated adducts thereof as friction reducing additives. U.S. Pat. No. 4,568,472 provides multifunctional additives for lubricating media which are borates of mixed ethoxylated amines and amides, hydroxyalkyl imidazolines, hydrolyzed hydroxyalkyl imidazolines and hydroxyesters.

U.S. Pat. No. 4,492,642 teaches lubricant additives which are the product of reacting a borating agent with an ammoniated hydrocarbyl epoxide.

U.S. Pat. No. 4,892,670 discloses boron-containing heterocyclic compounds prepared by reacting a primary amine or ammonia with an alkylene oxide or epoxide and then concurrently or subsequently the intermediate is reacted with a boric acid. The compounds are suitable antiwear additives for lubricating compositions.

U.S. Pat. No. 4,741,848 teaches boron containing compounds prepared by reacting hydroxy substituted esters, amides or imides with boric acid, boron trioxide, boron halides, boron amides or boron esters. The boron compounds are used as additives in lubricants and fuels.

Yao, J. and Dong, J. *Lubr. Eng.* 1995, 51(6), 475-8 and Zheng, Z., et al., *Wear* 1998, 222, 135-144) alkyl borates that contain nitrogen into the molecular structure.

It has been found that borates and boronate esters derived from 2-hydroxyethylpyridines, boric acids or boronic acids and hydrocarbyl alcohols provide excellent antiwear, extreme pressure, and friction modifiying additives for lubricating oils and fuels.

DETAILED DESCRIPTION

Disclosed are borate and boronate compounds of the formulae

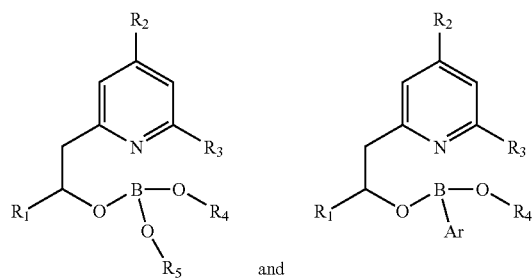

and where $R_1$, $R_2$ and $R_3$ are independently hydrogen, straight or branched chain alkyl of 1 to 24 carbon atoms, straight or branched chain alkenyl of 2 to 24 carbon atoms, cycloalkyl of 5 to 12 carbon atoms, aryl of 6 to 10 carbon atoms, aralkyl of 7 to 15 carbon atoms, alkaryl of 7 to 15 carbon atoms, Ar is substituted or unsubstituted aryl of 6 to 10 carbon atoms, and $R_4$ and $R_5$ are independently defined as for $R_1$ and may also be hydroxyphenyl or alkylated hydroxyphenyl, or $R_4$ and $R_5$ together with the —OBO— group form a substituted or unsubstituted 5 or 6 membered ring.

For example, $R_1$, $R_2$, $R_3$, $R_4$ and $R_5$ are independently hydrogen or straight or branched chain alkyl of 1 to 24 carbon atoms, aryl of 6 to 10 carbon atoms or alkaryl of 7 to 15 carbon atoms.

For instance, $R_4$ and $R_5$ are independently n-butyl, sec-butyl, t-butyl, n-dodecyl, n-octadecyl, n-octyl, isooctyl, oleyl, stearyl, n-tetradecyl, 1-hexadecyl, linoleyl, linolenyl, phytyl, myricyl, lauryl, myristyl, cetyl, behenyl, phenyl, catechyl, alkylated phenyl or alkylated hydroxyphenyl.

When $R_4$ and $R_5$ together with the —OBO— group form a substituted or unsubstituted 5 or 6 membered ring, the substituent is for example alkyl of 1 to 6 carbon atoms or is hydroxy. The ring may be substituted for example by 1 to 4 such groups.

Alkyl is straight or branched chain and is for example methyl, ethyl, n-propyl, iso-propyl, n-butyl, isobutyl, sec-butyl, t-butyl, n-pentyl, isopentyl, n-hexyl, n-heptyl, 3-heptyl, n-octyl, 2-ethylhexyl, n-nonyl, n-decyl, undecyl, n-dodecyl, tridecyl, n-tetradecyl, pentadecyl, n-hexadecyl, n-octadecyl, n-eicosyl, heptadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl and 1-methylundecyl.

Alkenyl is straight or branched chain and is unsaturated version of alkyl, for example allyl, prop-2-enyl, but-2-enyl, 2-methyl-prop-2-enyl, pent-2-enyl, hexa-2,4-dienyl, dec-10-enyl or eicos-2-enyl.

Cycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cyclodecyl, adamantyl, cyclododecyl, cycloheptyl or cyclooctyl.

Aralkyl is for example benzyl, alpha-methylbenzyl, alpha, alpha-dimethylbenzyl or 2-phenylethyl.

Aryl is for example phenyl or naphthyl. Substituted aryl is for example aryl substituted by 1 to 4 alkyl of 1 to 6 carbon atoms or hydroxyl groups.

Alkaryl is for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl, 2,6-diethylphenyl, 2,4-di-t-butylphenyl or 2,6-di-t-butyl-4-methylphenyl.

Hydroxyphenyl is for example 3-hydroxyphenyl.

Alkylated hydroxyphenyl is for example mono- or di-alkylated 3-hydroxyphenyl, for example 2-methyl-3-hydroxyphenyl, 4-methyl-3-hydroxyphenyl, 2-ethyl-3-hydroxyphenyl, 4-ethyl-3-hydroxyphenyl, 2-t-butyl-3-hydroxyphenyl, 4-t-butyl-3-hydroxyphenyl, 2-hexyl-3-hydroxyphenyl, 4-hexyl-3-hydroxyphenyl, 2,4-dimethyl-3-hydroxyphenyl, 2-methyl-4-t-butyl-3-hydroxyphenyl, and the other corresponding dialkylated versions. That is, the present compounds may be prepared with resorcinol or alkylated resorcinol.

The present compounds are for example prepared by the reaction of 2-hydroxyethylpyridines, boric acids or boronic acids and hydrocarbyl alcohols. For example, a present borate is prepared by the reaction of 2-hydroxyethylpyridine with boric acid and two equivalents of a hydrocarbyl alcohol, under conditions in which water is azeotropically removed. In a typical reaction, 1 equivalent of 2-(2-hydroxyethyl)pyridine, 2 equivalents of an alkanol (for example straight or branched chain $C_4$-$C_{18}$alkyl alcohol) and 1 equivalent of boric acid are heated together in an inert solvent under conditions such that water is azeotropically removed.

Boronates are similarly prepared, for example from the reaction of 2-(2-hydroxyethyl)pyridine, an arylboronic acid and 1 equivalent of an alkanol under conditions of the removal of water.

It is contemplated that a mixture of alkanols may be employed.

The solvent employed is for example toluene, xylene and the like. It is contemplated that under suitable conditions that the reaction may be run neat (no solvent).

Hydrocarbyl alcohols are for example 1-butanol, sec-butanol, t-butanol, 1-dodecanol, 1-octadecanol, 1-octanol, isooctanol, oleyl alcohol, stearic alcohol, 1-tetradecanol, 1-hexadecanol, linoleyl alcohol, linolenyl alcohol, phytol, myricyl alcohol, lauryl alcohol, myristyl alcohol, cetyl alcohol, behenyl alcohol, phenol, catechol, alkylated phenols, alkylated rescorcinols, ethylene glycol, propylene glycol, and the like.

The arylboronic acid is for example phenylboronic acid and the like.

Also subject of the present invention is a lubricant composition having improved antiwear properties comprising
  a) a lubricating oil and
  b) an antiwear enhancing amount of at least one compound selected from the group consisting of

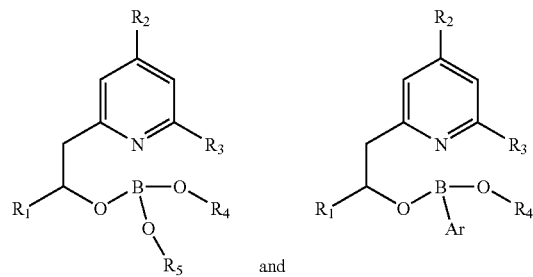

and where
$R_1$, $R_2$ and $R_3$ are independently hydrogen, straight or branched chain alkyl of 1 to 24 carbon atoms, straight or branched chain alkenyl of 2 to 24 carbon atoms, cycloalkyl of 5 to 12 carbon atoms, aryl of 6 to 10 carbon atoms, aralkyl of 7 to 15 carbon atoms, alkaryl of 7 to 15 carbon atoms, Ar is substituted or unsubstituted aryl of 6 to 10 carbon atoms, and $R_4$ and $R_5$ are independently defined as for $R_1$ and may also be hydroxyphenyl or alkylated hydroxyphenyl or $R_4$ and $R_5$ together with the —OBO— group form a substituted or unsubstituted 5 or 6 membered ring.

The present lubricating oils are for example those employed in internal combustion engines. The present oils have necessary lubricating viscosity. The oils are for example mineral oils or are synthetic and mixtures thereof.

Greases or other solid lubricants are also lubricating oils according to this invention.

The synthetic hydrocarbon oils include long chain alkanes such as cetanes and olefin polymers such as trimer and tetramers of octane and decene. These synthetic oils can be mixed with 1) ester oils such as pentaerythritol esters of monocarboxylic acids having about 2 to 20 carbon atoms, 2) polyglycol ethers, 3) polyacetals and 4) siloxane fluids. Useful among the synthetic esters are those made from polycarboxylic acids and monohydric alcohols. For example, ester fluids made from pentaerythritol or mixtures thereof with di- and tripentaerythritol, and an aliphatic monocarboxylic acid containing from 1 to 20 carbon atoms, or mixtures of such acids. Other examples are ester fluids made from trimethylolpropane and an aliphatic monocarboxylic acid containing from 1 to 20 carbon atoms, or mixtures of such acids.

The present lubricating oils are also for example crude oil, industrial lubrication oils, cutting oil, metal working fluids and greases.

Another use for the present borate and boronate additives is in fuels, for example certain aviation fuels and the like, wherein lubrication properties are desired. The fuels are for example a hydrocarbonaceous petroleum distillate such as motor gasoline, diesel fuel or fuel oil. Liquid fuel compositions comprising non-hydrocarbonaceous materials such as alcohols, ethers, organo-nitro compounds and the like (e.g. methanol, ethanol, diethyl ether, methyl ethyl ether, nitromethane) are also within the scope of this invention as are liquid fuels derived from vegetable or mineral sources such as corn, alfalfa, shale and coal. Fuels which are mixtures of one or more hydrocarbonaceous fuels and one or more non-hydrocarbonaceous materials are also contemplated. Examples of such mixtures are combinations of gasoline and ethanol and of diesel fuel and ether.

The present additives provide extreme pressure, antiwear and friction reducing properties to the oil, and upon combustion, are innocuous to conventional catalytic converters in automobiles.

The additives of this invention are advantageously present in the oil composition in an amount of for example about 0.01% to about 20% by weight of the total composition. For instance, the borates and boronates are present from about 0.05% to about 15%, from about 0.1% to about 10%, from about 0.2% to about 5% by weight, based on the weight of the entire composition. For example, the borates and boronates are present from about 0.1% to about 20%, from about 0.1% to about 15% or from about 0.1% to about 5% by weight, based on the weight of the entire composition.

It is contemplated that in lubricating compositions operated under extremely adverse conditions, such as lubricating compositions for marine diesel engines, that the additives of this invention may be present in amounts of up to about 30% by weight, or more, of the total weight of the lubricating composition.

The additives of this invention are advantageously present in the fuel compositions at a level of from about 1 ppm to about 50,000 ppm based on the fuel. For example the additives are present from about 4 ppm to about 5000 ppm based on the fuel.

The lubricating oils stabilized in accordance with the invention may additionally include other additives, which are added in order to improve still further the basic properties of these formulations; such additives include antioxidants, metal passivators, rust inhibitors, corrosion inhibitors, viscosity index improvers, extreme pressure agents, pour point depressants, solid lubricants, dispersants, detergents, antifoams, color stabilizers, further high-pressure additives, demulsifiers, antiwear additives and additives which reduce the coefficient of friction. Such additives are added in the customary amounts in each case in the range from in each case about 0.01% to 10.0% by weight, based on the lubricating oil.

The text below gives examples of such additional additives:

Examples of Antioxidants:

1) alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(a-methyl-cyclohexyl)-4,6-dimethylphenol, 2,6-di-octadecyl-4-methylphenol, 2,4,6-tricyclo-hexylphenol, 2,6-di-tert-butyl-4-methoxymethylphenol, linear or sidechain-branched nonylphenols, for example 2,6-di-nonyl-4-methylphenol, 2,4-dimethyl-6-(1'-methyl-undec-1'-yl)phenol, 2,4-dimethyl-6-(1'-methylheptadec-1'-yl)phenol, 2,4-dimethyl-6-(1'-methyltridec-1'-yl)phenol or mixtures thereof;

2) alkylthiomethylphenols, for example 2,4-di-octylthiomethyl-6-tert-butylphenol, 2,4-di-octylthiomethyl-6-methylphenol, 2,4-di-octylthiomethyl-6-ethylphenol or 2,6-di-dodecylthiomethyl-4-nonylphenol;

3) hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate or bis(3,5-di-tert-butyl-4-hydroxyphenyl) adipate;

4) tocopherols, for example α-, β-, γ- or δ-tocopherol or mixtures thereof (vitamin E);

5) hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis-(6-tert-butyl-2-methylphenol), 4,4'-thiobis(3,6-di-sec-amylphenol) or 4,4'-bis(2,6-dimethyl-4-hydroxyphenyl) disulfide;

6) alkylidenebisphenols, for example 2,2'-methylenebis(6-tert-butyl-4-methylphenol), 2,2'-methylenebis(6-tert-butyl-4-ethylphenol), 2,2'-methylenebis(4-methyl-6-(alphamethylcyclohexyl)-phenol), 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis(6-(alpha-methylbenzyl)-4-nonylphenol), 2,2'-methylenebis(6-(alpha,alpha-dimethylbenzyl)-4-nonylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis(3,3-bis(3'-tert-butyl-4'-hydroxyphenyl) butyrate), bis(3-tert-butyl-4-hydroxy-5-methylphenyl)dicyclo-pentadiene, bis(2-(3'-tert-butyl-2'-hydroxy-5'-methylbenzyl)-6-tert-butyl-4-methylphenyl)terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane or 1,1,5,5-tetra(5-tert-butyl-4-hydroxy-2-methylphenyl)-pentane;

7) O- N- and S-benzyl compounds, for example 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl)amine, bis(4-tert-butyl-3-hydroxy-2,6-dimethylbenzyl)dithioterephthalate, bis(3,5-di-tert-butyl-4-hydroxybenzyl)sulfide or isooctyl 3,5-di-tert-butyl-4-hydroxybenzylmercaptoacetate;

8) hydroxybenzylated malonates, for example-dioctadecyl 2,2-bis(3,5-di-tert-butyl-2-hydroxybenzyl)malonate, dioctadecyl 2-(3-tert-butyl-4-hydroxy-5-methylbenzyl)-malonate, di-dodecyl mercaptoethyl-2,2-bis(3,5-di-tert-butyl-4-hydroxybenzyl)-malonate or di(4-(1,1,3,3-tetramethylbutyl)phenyl)2,2-bis(3,5-di-tert-butyl-4-hydroxybenzyl) malonate;

9) aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene or 2,4,6-tris(3,5-di-tert-butyl-4-hydroxybenzyl)phenol;

10) triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)-isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine or 1,3,5-tris(3,5-dicyclohexyl-4-hydroxybenzyl)-isocyanurate;

11) benzylphosphonates, for example dimethyl 2,5-di-tert-butyl-4-hydroxybenzyl-phosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate or the calcium salt of the monoethyl ester of 3,5-di-tert-butyl-4-hydroxybenzylphosphonic acid;

12) acylaminophenols, for example 4-hydroxylauranilide, 4-hydroxystearanilide or octyl N-(3,5-di-tert-butyl-4-hydroxyphenyl)carbamate;

13) esters of β-(3,5-di-tert-butyl-4-hydroxyphenyl)propionic acid, β-(5-tert-butyl-4-hydroxy-3-methylphenyl)propionic acid, β-(3,5-dicyclohexyl-4-hydroxyphenyl)-propionic acid, 3,5-di-tert-butyl-4-hydroxyphenylacetic acid or β-(5-tert-butyl-4-hydroxyphenyl)-3-thiabutyric acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethyl-hexanediol, trimethylolpropane, 4-hydroxymethyl-1-phospha-2,6,7-trioxabicyclo(2.2.2)octane, glycerol or transesterification products based on natural triglycerides of, for example, coconut oil, rape seed oil, sunflower oil or colza oil;

14) amides of β-(3,5-di-tert-butyl-4-hydroxyphenyl)propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine or N,N'-bis(3,5-di-tert-butyl-4-hydroxyphenylpropionyl)hydrazine;

15) ascorbic acid (vitamin C);

16) amine-type antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylendiamine, N,N'-dicyclohexyl-p-phenylenediamine, N,N'-diphenyl-p-phenylenediamine, N,N'-di-(naphth-2-yl)-p-phenylenediamine, N-isopropyl-N'-phenyl-p-phenylenediamine, N-(1,3- dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, e.g. p,p'-di-tert-octyidiphenyl-amine, 4-n-butylaminophenol, 4-butyrylamino-phenol, 4-nonanoylamino-phenol, 4-dodecanoylaminophenol, 4-octadecanoylamino-phenol, di-(4-methoxyphenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-((2-methyl-phenyl)-amino)-ethane, 1,2-di-(phenylamino)propane, (o-tolyl) biguanide, di(4-(1',3'-dimethyl-butyl)-phenyl)amine, tert-octylated N-phenyl-1-naphthylamine, a mixture of mono- and dialkylated tert-butyl/tert-octyidiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, mixtures of mono- and dialkylated tert-butyidiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octyl-phenothiazines, N-allylphenothiazine, N,N,N',N'-tetraphenyl-1,4-diaminobut-2-ene, N,N-bis-(2,2,6,6-tetramethylpiperidin-4-yl)hexamethylenediamine, bis-(2,2,6,6-tetramethylpiperidin-4-yl) sebacate, 2,2,6,6-tetramethylpiperidin-4-one or 2,2,6,6-tetramethylpiperidin-4-ol; and 17) aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,1-trithiatridecane or 2,2,15,15-tetramethyl-5,12-dihydroxy-3,7,10,14-tetrathiahexadecane.

Examples of Metal Passivators, for Example for Copper, are:
1) benzotriazoles and their derivatives, for example 4- or 5-alkylbenzotriazoles (e.g. tolutriazole) and derivatives thereof, 4,5,6,7-tetrahydrobenzotriazole, 5,5'-methylenebisbenzotriazole; Mannich bases of benzotriazole or tolutriazole, such as 1-(di(2-ethylhexyl)aminomethyl)tolutriazole and 1-(di(2-ethylhexyl)aminomethyl)-benzotriazole; alkoxyalkylbenzotriazoles, such as 1-(nonyloxymethyl)-benzotriazole, 1-(1-butoxyethyl)-benzotriazole and 1-(1-cyclohexyloxybutyl)-tolutriazole;

2) 1,2,4-triazoles and derivatives thereof, for example 3-alkyl(or aryl)-1,2,4-triazoles, Mannich bases of 1,2,4-triazoles such as 1-(di(2-ethylhexyl)aminomethyl)-1,2,4-triazole; alkoxyalkyl-1,2,4-triazoles such as 1-(1-butoxyethyl)-1,2,4-triazole; acylated 3-amino-1,2,4-triazoles;

3) imidazole derivatives, for example 4,4'-methylenebis (2-undecyl-5-methyl-imidazole), bis((N-methyl)imidazol-2-yl)carbinol octyl ether;

4) sulfur-containing heterocyclic compounds, for example 2-mercaptobenzothiazole, 2,5-dimercapto-1,3,4-thiadiazole, 2,5-dimercaptobenzothiadiazole and derivatives thereof; 3,5-bis(di(2-ethylhexyl)aminomethyl)-1,3,4-thiadiazolin-2-one; and 5) amino compounds, for example salicylidenepropylenediamine, salicylaminoguanidine and salts thereof.

Examples of Rust Inhibitors are:
1) organic acids, their esters, metal salts, amine salts and anhydrides, for example alkyl- and alkenylsuccinic acids and the partial esters thereof with alcohols, diols or hydroxycarboxylic acids, partial amides of alkyl- and alkenylsuccinic acids, 4-nonylphenoxyacetic acid, alkoxy- and alkoxyethoxycarboxylic acids, such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(2-carboxyethyl)-1-dodecyl-3-methylglycerine and its salts, especially sodium and triethanolamine salts;

2) nitrogen-containing compounds, for example:
i) primary, secondary or tertiary aliphatic or cycloaliphatic amines and amine salts of organic and inorganic acids, for example oil-soluble alkylammonium carboxylates, and also 1-(N,N-bis(2-hydroxyethyl)amino)-3-(4-nonylphenoxy)propan-2-ol;
ii) heterocyclic compounds, for example: substituted imidazolines and oxazolines, 2-heptadecenyl-1-(2-hydroxyethyl)-imidazoline;

3) phosphorus-containing compounds, for example Amine salts of phosphoric acid partial esters or phosphonic acid partial esters, zinc dialkyldithiophosphates;

4) sulfur-containing compounds, for example: barium dinonylnaphthalene-sulfonates, calcium petroleumsulfonates, alkylthio-substituted aliphatic carboxylic acids, esters of aliphatic 2-sulfocarboxylic acids and salts thereof; and 5) glycerine derivatives, for example: glycerine monooleate, 1-(alkylphenoxy)-3-(2-hydroxyethyl)glycerines, 1-(alkylphenoxy)-3-(2,3-dihydroxypropyl)glycerines, 2-carboxyalkyl-1,3-dialkylglycerines.

Examples of Viscosity Index Improvers are:
polyacrylates, polymethacrylates, vinylpyrrolidone/methacrylate copolymers, polyvinylpyrrolidones, polybutenes, olefin copolymers, styrene/acrylate copolymers, polyethers.

Examples of Pour Point Depressants are:
polymethacrylate, alkylated naphthalene derivatives.

Examples of Dispersants/Surfactants are:
polybutenylsuccinamides or -imides, polybutenylphosphonic acid derivatives, and basic magnesium, calcium and barium sulfonates, phenolates and salicylates.

Examples of Antifoams are: Silicone Oils and Polymethocrylen.

The Demulsifiers are for Example Selected from:
polyetherpolyols and dinonylnaphthalenesulfonates.

The Friction Modifiers are for Example Selected from:
fatty acids and their derivatives (i.e. natural esters of fatty acids such as glycerol monooleate), amides, imides and amines (i.e. oleylamine), sulfur containing organomolybdenum dithiocarbamates, sulfur-phosphorus containing organomolybdenum dithiophosphates, sulfur-nitrogen containing organomolybdenum compounds based on dispersants, molybdenum carboxylate salts, molybdenum-amine complexes, molybdenum amine/alcohol/amid complexes and molybdenum cluster compounds, Teflon™ and molybdenum disulfide.

Examples of Additional Antiwear Additives are:
sulfur- and/or phosphorus- and/or halogen-containing compounds, such as sulfurized olefins and vegetable oils, zinc dialkyldithiophosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, di-(2-ethylhexyl)-aminomethyltolyltriazole, derivatives of 2,5-dimercapto-1,3,4-thiadiazole, ethyl(bisisopropyloxyphosphinothioyl)thiopropionate, triphenyl thiophosphate (triphenyl phosphorothioate), tris(alkylphenyl) phosphorothioates and mixtures thereof (for example tris(isononylphenyl) phosphorothioate), diphenylmononylphenyl phosphorothioate, isobutylphenyl diphenyl phosphorothioate, the dodecylamine salt of 3-hydroxy-1,3-thiaphosphetan 3-oxide, trithiophosphoric acid 5,5,5-trisisooctyl 2-acetate, derivatives of 2-mercaptobenzothiazole, such as 1-N,N-bis(2-ethylhexyl)aminomethyl-2-mercapto-1 H-1,3-benzothiazole, and ethoxycarbonyl 5-octyldithiocarbamate;

dihydrocarbyl dithiophosphate metal salts where the metal is aluminum, lead, tin manganese, cobalt, nickel, zinc or copper, but most often zinc. The zinc salt (zinc dialkyl dithiophosphate) is represented as

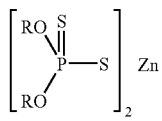

where R and R' are independently $C_1$-$C_{20}$ alkyl, $C_3$-$C_{20}$ alkenyl, $C_5$-$C_{12}$ cycloalkyl, $C_7$-$C_{13}$ aralkyl or $C_6$-$C_{10}$ aryl, for example R and R' are independently $C_1$-$C_{12}$ alkyl;

antiwear additives as described in U.S. Pat. Nos. 4,584,021; 5,798,321; 5,750,478; 5,801,130; 4,191,666; 4,720,288; 4,025,288; 4,025,583 and WO 095/20592, which U.S. patents are incorporated herein by reference; amines for example polyalkylene amines such as ethylene diamine, diethylene triamine, triethylene tetraamine, tetraethylene pentamine, pentaethylene hexamine, nonaethylene decamine and aryl amines as described in U.S. Pat. No. 4,267,063, herein incorporated by reference; salts of amine phosphates comprising specialty amines and mixed mono- and di-acid phosphates; the mono- and di-acid phosphate amines have the structural formulae:

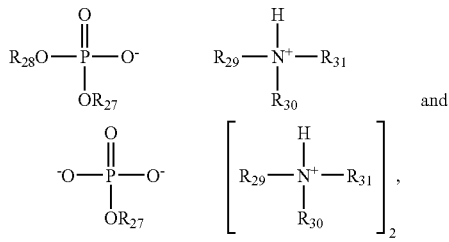

wherein $R_{27}$ is hydrogen, $C_1$-$C_{25}$ linear or branched chain alkyl which is unsubstituted or substituted by one or more $C_1$-$C_6$alkoxy groups, a saturated acyclic or alicyclic group, or aryl;

$R_{28}$ is $C_1$-$C_{25}$ linear or branched chain alkyl which is unsubstituted or substituted by one or more $C_1$-$C_6$alkoxy groups, a saturated acyclic or alicyclic group, or aryl;

$R_{29}$ is hydrogen, $C_1$-$C_{25}$ linear or branched chain alkyl, a saturated or unsaturated acyclic or alicyclic group, or aryl; and are hydrogen or $C_1$-$C_{12}$ linear or branched chain alkyl; and $R_{30}$ and $R_{31}$, are, each independently of the other, $C_1$-$C_{25}$ linear or branched chain alkyl, a saturated or unsaturated acyclic or alicyclic group, or aryl. Preferably, $R_{27}$ and $R_{28}$ are linear or branched $C_1$-$C_{12}$ alkyl; and $R_{29}$, $R_{30}$ and $R_{31}$, are linear or branched $C_1$-$C_{18}$ alkyl;

IRGALUBE 349 (Ciba Specialty Chemicals) has been found to be very useful, particularly by enhancing the wear performance of the base oil such that it meets stringent military performance specifications; IRGALUBE 349 has the formula

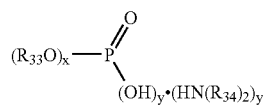

wherein $R_{33}$ is n-hexyl, $R_{34}$ is $C_{11}$-$C_{14}$ branched alkyl, and when x=1 then y=2; when x=2 then y=1; Irgalube® 349 is a mixture of amine phosphates, CAS #80939-62-4;

other conventional antiwear additives are compounds of the formula

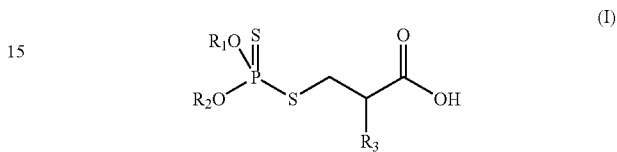

in which $R_1$ and $R_2$ independently of one another are $C_3$-$C_{18}$ alkyl, $C_5$-$C_{12}$ cycloalkyl, $C_5$-$C_6$ cycloalkylmethyl, $C_9$-$C_{10}$ bicycloalkylmethyl, $C_9$-$C_{10}$ tricycloalkylmethyl, phenyl or $C_7$-$C_{24}$ alkylphenyl or together are $(CH_3)_2C(CH_2)_2$, $R_3$ is hydrogen or methyl. For example, Irgalube® 353, a dialkyl dithiophosphate ester, CAS #268567-32-4, Ciba Specialty Chemicals.

The present fuel compositions can contain, in addition to the borate and boronate additives, other additives which are well known to those of skill in the art. These include antiknock agents such as tetralkyl lead compounds, lead scavengers such as haloalkanes (e.g., ethylene dichloride and ethylene dibvromide), deposit preventers or modifiers such as triaryl phosphates, dyes, cetane improvers, antioxidants such as 2,6-di-tert-butyl-4-methylphenol, rust inhibitors such as alkylated succinic acids and anhydrides, bacteriostatic agents, gum inhibitors, metal deactivators, demulsifiers, upper cylinder lubircants and anti-icing agents.

The present borates and boronates can be introduced into the lubricating oil in manners known per se. The compounds are readily soluble in oils. They may be added directly to the lubricating oil or they can be diluted with a substantially inert, normally liquid organic diluent such as naphtha, benzene, toluene, xylene or a normally liquid oil or fuel to form an additive concentrate or masterbatch. These concentrates generally contain from about 10% to about 90% by weight additive and may contain one or more other additional additives. The present borates and boronates may be introduced as part of an additive package.

The present invention is further illustrated by the following Examples:

EXAMPLE 1 di-(n-dodec-1-yl)-(2-(pyridin-2-yl)ethyl) borate

A 500 mL glass reaction vessel equipped with a magnetic stir bar and Dean-Stark tube fitted with a reflux condenser is charged with 12.3 g of 2-(2-hydroxyethyl)pyridine, 37.2 g of 1-dodecanol, 6.2 g of boric acid and 250 mL of toluene. The mixture is stirred and heated at reflux for 5 hours, during which time ca. 5 mL of water is removed, indicating ester formation. The solution is filtered to remove haziness, the solvent is removed by vacuum distillation, and the borate ester is obtained as a clear pale-yellow oil.

EXAMPLE 2 n-octadec-1-yl-(2-(pyridin-2-yl)ethyl phenylboronate

A 200 mL glass reaction vessel equipped with a magnetic stir bar and Dean-Stark tube fitted with a reflux condenser is charged with 5.69 mL of 2-(2-hydroxyethyl)pyridine, 13.7 g of 1-octadecanol, 6.29 g of phenylboronic acid, and 150 mL of toluene. The mixture is stirred and heated at reflux for 16 hours, during which time 1.8 mL of water is removed, indicating ester formation. The solution is filtered to remove haziness and the solvent removed by vacuum distillation, resulting in 23.4 g of a pale yellow oil which solidifies to a waxy substance on cooling.

EXAMPLE 3 n-oct-1-yl-(pyridin-2-yl)ethyl phenylboronate

A 200 mL glass reaction vessel equipped with a magnetic stir bar and Dean-Stark tube fitted with a reflux condenser is charged with 5.69 mL of 2-(2-hydroxyethyl)pyridine, 7.96 g of 1-octanol, 6.29 g of phenylboronic acid, and 150 mL of toluene. The mixture is stirred and heated at reflux for 16 hours, during which time 1.8 mL of water is removed, indicating ester formation. The solution is filtered to remove haziness and the solvent removed by vacuum distillation, resulting in 16 g of a viscous dark yellow oil.

EXAMPLE 4 n-ole-1-yl-(2-(pyridin-2-yl)ethyl phenylboronate

A 200 mL glass reaction vessel equipped with a magnetic stir bar and Dean-Stark tube fitted with a reflux condenser is charged with 5.69 mL of 2-(2-hydroxyethyl)pyridine, 18.6 mL of oleyl alcohol, 6.29 g of phenylboronic acid, and 150 mL of toluene. The mixture is stirred and heated at reflux for 16 hours, during which time 1.8 mL of water is removed, indicating ester formation. The solvent is removed by vacuum distillation, resulting in 24 g of a viscous dark yellow oil.

EXAMPLE 5 di-(n-oct-1-yl)-(2-(pyridin-2-yl)ethyl) borate

A 2000 mL glass reaction vessel equipped with a magnetic stir bar and Dean-Stark tube fitted with a reflux condenser is charged with 75.0 g of 2-(2-hydroxyethyl) pyridine, 158.7 g of 1-octanol, 61.8 g of boric acid and 1500 mL of toluene. The mixture is stirred and heated at reflux for 18 hours, during which time ca. 33 mL of water is removed, indicating ester formation. The solution is filtered to remove haziness, the solvent is removed by vacuum distillation, and the resulting oil is filtered through a glass frit to give the borate ester as a clear pale-yellow oil.

EXAMPLE 6

Antiwear Properties

Antiwear properties are measured on a PCS Instruments Mini-Traction Machine, modified with a Pin-on-Disc attachment, in which a stationary pin (500×500 microns) is held against a rotating disc, with a fixed load applied at a constant temperature. Wear is measured as the displacement of the pin, due to loss of material from the pin. The test oil is a zero S, very low P automotive engine oil, fully formulated except that no antiwear additive is included. The reaction test conditions are 10N load, oil temperature 100° C. Wear data is recorded for 60 min, and the average wear rate is reported here as the linear regression slope of the wear curve. Additives are reported in weight percent based on the formulated oil.

| Oil | Wear Rate |
| --- | --- |
| Control (no antiwear additive) | 279 microns/hour |
| + 1.2% ZDDP | 3.0 microns/hour |
| + 1% compound of Ex. 1 | 5.7 microns/hour |

ZDDP is zinc dialkyl dithiophosphate - a secondary ZDDP at 1.2% provides 0.1% P.

EXAMPLE 7

Four Ball Antiwear Testing

Antiwear properties of the borate esters of the present invention are tested at a level of 1.0 wt % in a test oil. The test oil is a P-free, very low S automotive engine oil, fully formulated except that no antiwear additive is included in the formulation. The antiwear properties are determined in the Four-Ball Wear Test under ASTM D 1472 test conditions, using a 40 kg (392 N) load. The test is run in duplicate, and the test results, Average Wear Scar Diameter (mm) are reported. The numerical value of the test results decreases with an increase of effectiveness of the additive.

| Compound | Avg Wear Scar Diameter (mm) |
| --- | --- |
| test oil (no antiwear additive) | 0.675 |
| test oil + 1% Compound of Ex. 1 | 0.65 |
| test oil + 1% Compound Ex. 5 | 0.615 |
| test oil + 1% ZDDP | 0.61 |

What is claimed is:

1. A borate or boronate compound selected from the group consisting of

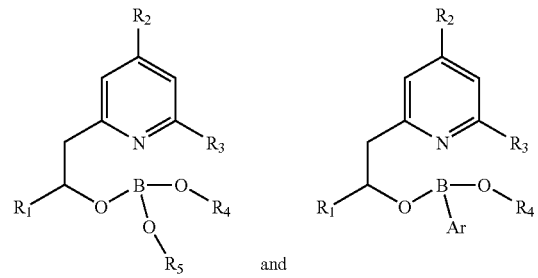

and where $R_1$, $R_2$ and $R_3$ are independently hydrogen, straight or branched chain alkyl of 1 to 24 carbon atoms, straight or branched chain alkenyl of 2 to 24 carbon atoms, cycloalkyl of 5 to 12 carbon atoms, aryl of 6 to 10 carbon atoms, aralkyl of 7 to 15 carbon atoms, alkaryl of 7 to 15 carbon atoms, Ar is substituted or unsubstituted aryl of 6 to 10 carbon atoms, and $R_4$ and $R_5$ are independently defined as for $R_1$ or may also be hydroxyphenyl or alkylated hydroxyphenyl.

2. A compound according to claim 1 of the formula

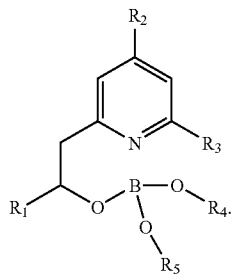

3. A compound according to claim 1 of the formula

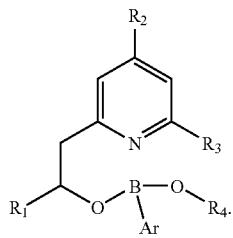

4. A compound according to claim 1 in which $R_1$, $R_2$, $R_3$, $R_4$ and $R_5$ are independently hydrogen or straight or branched chain alkyl of 1 to 24 carbon atoms, aryl of 6 to 10 carbon atoms or alkaryl of 7 to 15 carbon atoms.

5. A compound according to claim 1 in which $R_4$ and $R_5$ are independently n-butyl, sec-butyl, t-butyl, n-dodecyl, n-octadecyl, n-octyl, isooctyl, oleyl, stearyl, n-tetradecyl, 1-hexadecyl, linoleyl, linolenyl, phytyl, myricyl, lauryl, myristyl, cetyl, behenyl, phenyl, catechyl, alkylated phenyl or alkylated hydroxyphenyl.

6. A compound according to claim 1 which is di-(n-dodec-1-yl)-(2-(pyridin-2-yl)ethyl) borate, n-octadec-1-yl-(2-(pyridin-2-yl)ethyl phenylboronate, n-oct-1-yl-(2-(pyridin-2-yl)ethyl phenylboronate or n-ole-1-yl-(2-(pyridin-2-yl)ethyl phenylboronate.

7. A lubricant composition having improved antiwear properties comprising
 a) a lubricating oil and
 b) an antiwear enhancing amount of at least one compound selected from the group consisting of

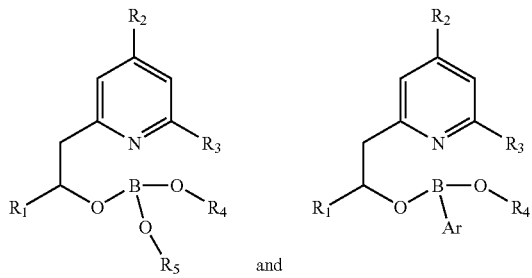

and where
 $R_1$, $R_2$ and $R_3$ are independently hydrogen, straight or branched chain alkyl of 1 to 24 carbon atoms, straight or branched chain alkenyl of 2 to 24 carbon atoms, cycloalkyl of 5 to 12 carbon atoms, aryl of 6 to 10 carbon atoms, aralkyl of 7 to 15 carbon atoms, alkaryl of 7 to 15 carbon atoms,
 Ar is substituted or unsubstituted aryl of 6 to 10 carbon atoms, and
 $R_4$ and $R_5$ are independently defined as for $R_1$ or may also be hydroxyphenyl or alkylated hydroxyphenyl.

8. A composition according to claim 7 comprising at least one compound of the formula

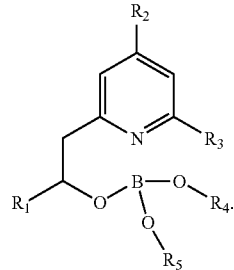

9. A composition according to claim 7 comprising at least one compound of the formula

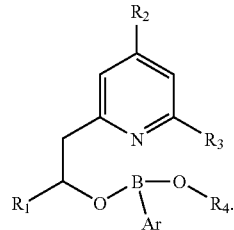

10. A composition according to claim 7 in which $R_1$, $R_2$, $R_3$, $R_4$ and $R_5$ are independently hydrogen or straight or branched chain alkyl of 1 to 24 carbon atoms, aryl of 6 to 10 carbon atoms or alkaryl of 7 to 15 carbon atoms.

11. A composition according to claim 7 in which $R_4$ and $R_5$ are independently n-butyl, sec-butyl, t-butyl, n-dodecyl, n-octadecyl, n-octyl, isooctyl, oleyl, stearyl, n-tetradecyl, 1-hexadecyl, linoleyl, linolenyl, phytyl, myricyl, lauryl, myristyl, cetyl, behenyl, phenyl, catechyl, alkylated phenyl or alkylated hydroxyphenyl.

12. A composition according to claim 7 comprising di-(n-dodec-1-yl)-(2-(pyridin-2-yl)ethyl) borate, n-octadec-1-yl-(2-(pyridin-2-yl)ethyl phenylboronate, n-oct-1-yl-(2-(pyridin-2-yl)ethyl phenylboronate or n-ole-1-yl-(2-(pyridin-2-yl)ethyl phenylboronate.

13. A composition according to claim 7 where the lubricating oil is a mineral oil.

14. A composition according to claim 7 where the lubricating oil is a synthetic oil.

15. A composition according to claim 7 where the lubricating oil is a mixture of synthetic and mineral oils.

16. A composition according to claim 7 where the lubricating oil is a grease or other solid lubricant.

17. A composition according to claim 7 in which component b) is present from about 0.01% to about 20% by weight, based on the total composition.

18. A composition according to claim 7 in which component b) is present from about 0.2% to about 5% by weight, based on the total composition.

19. A composition according to claim 7 comprising further additives selected from the group consisting of the antioxidants, metal passivators, rust inhibitors, corrosion inhibitors, viscosity index improvers, extreme pressure agents, pour point depressants, solid lubricants, dispersants, detergents, antifoams, color stabilizers, further high-pressure additives, demulsifiers, antiwear additives and additives which reduce the coefficient of friction.

20. A composition according to claim 7 which is an additive concentrate where component b) is present from about 10% to about 90% by weight, based on the total composition.

* * * * *